(12) United States Patent
Johnson

(10) Patent No.: US 8,845,978 B2
(45) Date of Patent: Sep. 30, 2014

(54) DETECTION KIT

(71) Applicant: Field Forensics, Inc., St. Petersburg, FL (US)

(72) Inventor: Craig Richard Johnson, Tierra Verde, FL (US)

(73) Assignee: Field Forensics, Inc., St. Petersburg, FL (US)

( * ) Notice: Subject to any disclaimer, the term of this patent is extended or adjusted under 35 U.S.C. 154(b) by 0 days.

(21) Appl. No.: 13/782,912

(22) Filed: Mar. 1, 2013

(65) Prior Publication Data

US 2014/0093969 A1    Apr. 3, 2014

Related U.S. Application Data

(63) Continuation of application No. PCT/US2011/053925, filed on Sep. 29, 2011.

(60) Provisional application No. 61/388,168, filed on Sep. 30, 2010.

(51) Int. Cl.
| | |
|---|---|
| *B01L 3/00* | (2006.01) |
| *G01N 31/22* | (2006.01) |
| *G01N 33/52* | (2006.01) |
| *G01N 21/78* | (2006.01) |
| *C12M 1/34* | (2006.01) |
| *C12M 3/00* | (2006.01) |
| *G01N 1/02* | (2006.01) |

(52) U.S. Cl.
CPC .......... *G01N 21/78* (2013.01); *G01N 2001/028* (2013.01); *G01N 1/02* (2013.01)
USPC ......... 422/430; 422/406; 422/411; 435/287.7

(58) Field of Classification Search
CPC .... B01L 2200/16; B01L 3/5029; C12M 1/30; G01N 2001/028; Y10S 435/81
USPC ........ 422/406, 411, 430; 435/287.7; 206/361; 401/129; 604/1
See application file for complete search history.

(56) References Cited

U.S. PATENT DOCUMENTS

4,562,043 A * 12/1985 Mennen et al. ............... 422/411
5,055,258 A * 10/1991 Brodt et al. ................... 422/408
(Continued)

*Primary Examiner* — Bobby Ramdhanie
*Assistant Examiner* — Bryan Kilpatrick
(74) *Attorney, Agent, or Firm* — Christopher Paradies; Paradies Law P.A.

(57) ABSTRACT

A detection kit comprises a plurality of swabs, each of the plurality of swabs having the form of a stick, being bundled together in a single test kit for detection of a plurality of chemical compounds. A user opens a detection kit, swabs a surface or surfaces with the bundled sticks, collecting chemical constituents to be tested on detection surfaces of each of the plurality of sticks. Liquids, mists, vapors and powders may be tested in one method, utilizing one or more dry reagents on the detection surfaces. The sticks may comprise a volume of fluid, releasably contained within the sticks, such that when activated, a fluid, such as a reagent or solvent, is wicked by a wicking tip to the detection surface of the stick. For example, a mechanism is provided that is capable of breaking a vial or ampoule containing the fluid, when activated by a twisting motion or compression. Adhesive may be present on one or more of the detection surfaces. A transparent reaction chamber may be provided by a transparent cover or cap.

21 Claims, 21 Drawing Sheets

(56) References Cited

U.S. PATENT DOCUMENTS

| | | |
|---|---|---|
| 5,078,968 A | 1/1992 | Nason |
| 6,248,294 B1 * | 6/2001 | Nason ............................ 422/411 |
| 6,991,898 B2 * | 1/2006 | O'Connor ......................... 435/4 |
| 8,585,982 B1 * | 11/2013 | Quintana et al. ............... 422/413 |
| 2005/0084842 A1 | 4/2005 | O'Connor |
| 2005/0131314 A1 | 6/2005 | Hird et al. |
| 2008/0286831 A1 | 11/2008 | Liang |
| 2012/0220042 A1 * | 8/2012 | Sangha ......................... 436/174 |

\* cited by examiner

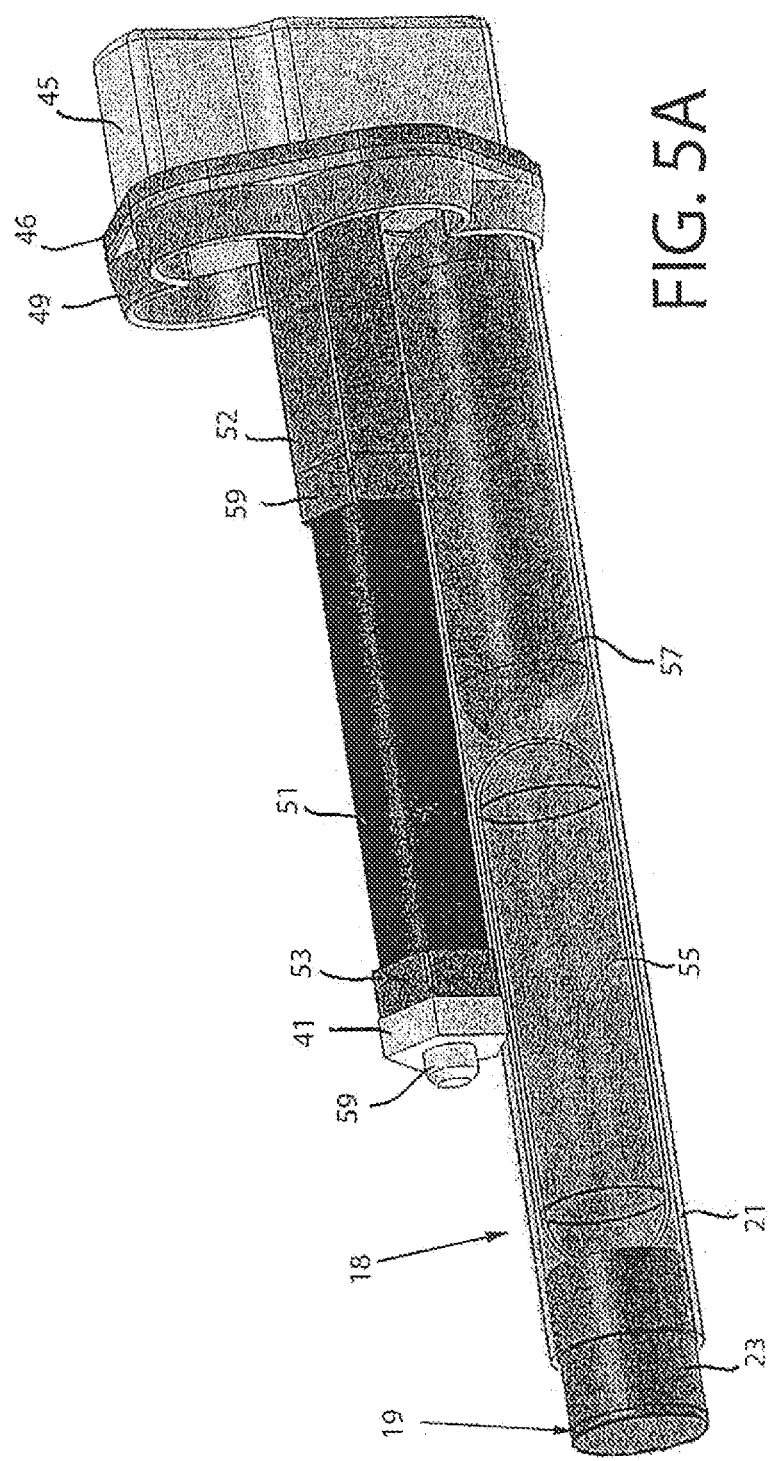

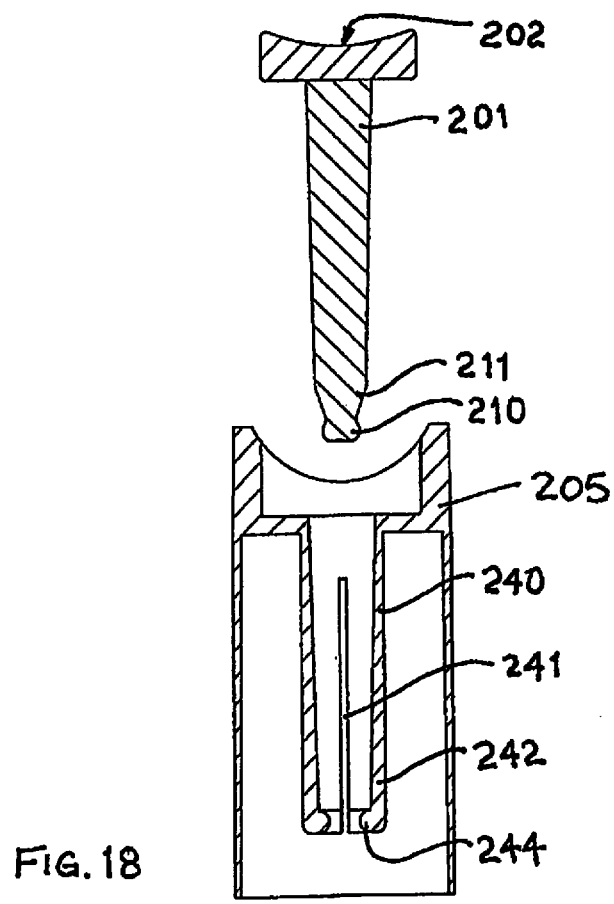
FIG. 18
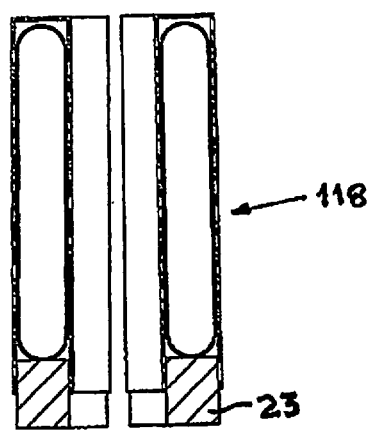
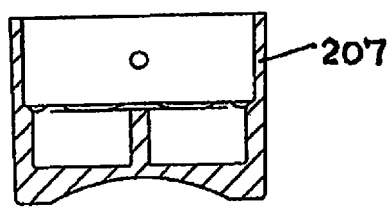

DETECTION KIT

RELATED APPLICATION

This application is a continuation of PCT/US2011/053925 filed Sep. 29, 2011 which claims the benefit of U.S. provisional application No. 61/388,168 filed Sep. 30, 2010 the disclosures of which are hereby incorporated herein by reference in their entirety.

FIELD OF INVENTION

The field relates to detection kits using reagents for detection of chemical compounds, such as drugs and explosive compounds, for example.

BACKGROUND

Detection kits are known that use reagents for detecting chemical compounds by changes in contrast, color or the like. A variety of reagents are very well known for detecting one or more chemical compounds or classes of chemical compounds.

SUMMARY OF INVENTION

A detection kit comprises a plurality of swabs, each of the plurality of swabs having the form of a stick, being bundled together in a single test kit for detection of a plurality of chemical compounds. For example, five detection sticks are bundled together in a single test kit. A user can open the kit, swab a surface or surfaces with the bundled sticks, collecting chemical constituents to be tested, such as powders, on the detection surfaces of each of the sticks, enclose the bundled sticks into a reaction chamber, and rupture an ampoule in the reaction chamber to release a fluid that initiates a chemical reaction at the detection surface, if compounds to be detected are present on one or more of the detection surfaces. For example, an adhesive is present on one or more of the detection surfaces that allows easy collection of powders from a surface to be swabbed.

In one example, the detection kit has a transparent reaction chamber or transparent cover, allowing the user of the kit to observe any color change on the detection surfaces. For example, a transparent cover may be placed over the detection surfaces of the bundled sticks, enclosing the bundled sticks within the reaction chamber without obscuring a view of the detection surfaces. In one example, the transparent cover may be locked into place once the bundled sticks are enclosed by the cover inside of the reaction chamber. In an alternative example, a mechanism for rupturing of an ampoule in the reaction chamber locks the transparent cover in place, as well, sealing the bundled sticks within the reaction chamber.

BRIEF DESCRIPTION OF THE DRAWINGS

The examples illustrated in the following drawings and the detailed description are examples of the invention for the purpose of illustrating features of the invention to be recited in the claims of an issued patent and are not limiting to the scope of the inventions claimed.

FIGS. 5A and 5B illustrate a single detection stick disposed in relation to a rotary mechanism shown in (A) a partial cutaway view and (B) a partially exploded cutaway view, which is similar to the examples in FIGS. 4A and 4B, except in FIG. 5 the rotary mechanism is design to rupture two ampoules in each detection stick by forcing both the top and bottom portions of the segmented rupture mechanism to spread outwardly.

FIG. 18 illustrates a partial cross-sectional view of the exploded view in FIG. 17.

DETAILED DESCRIPTION

Figure 1:
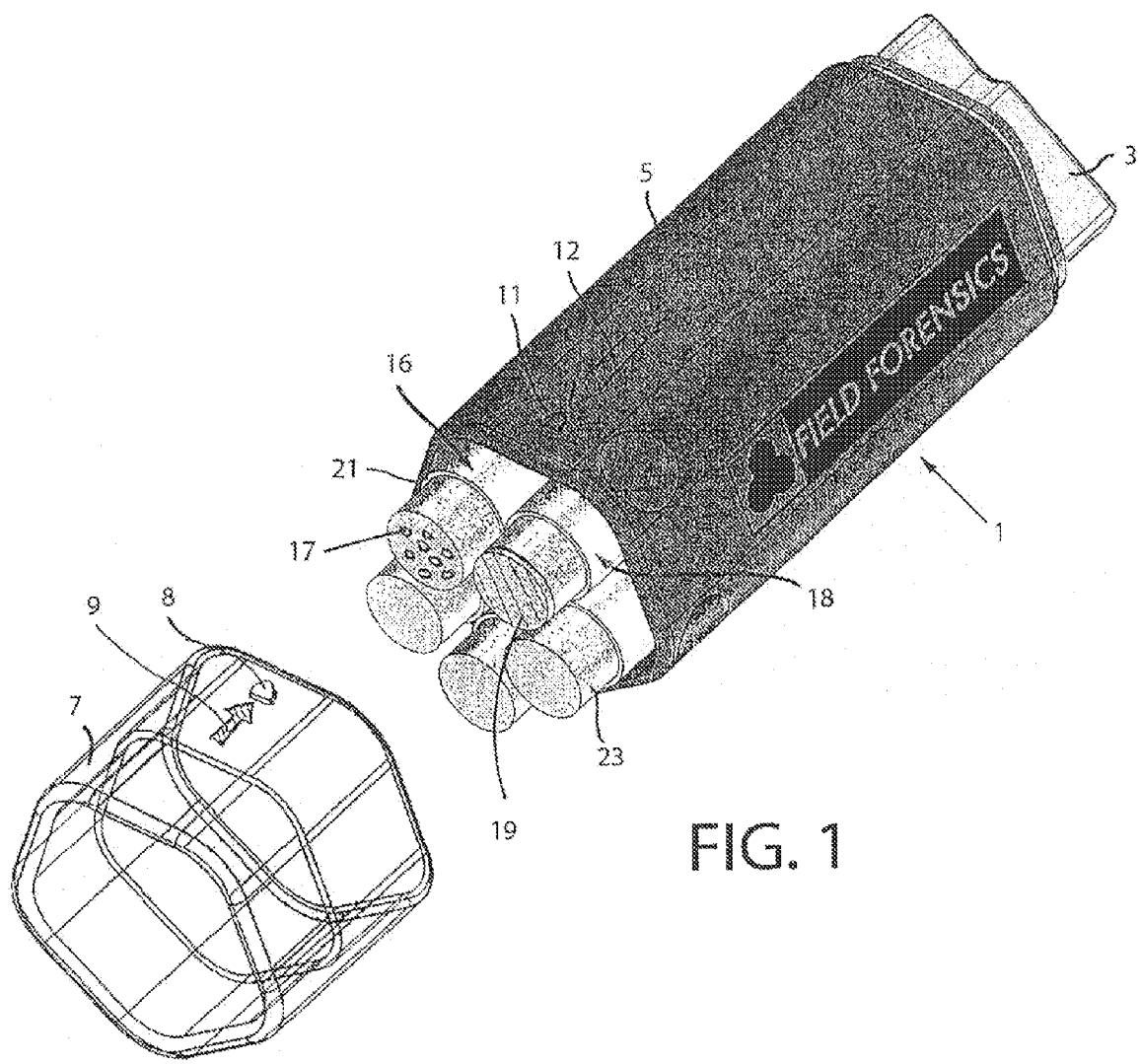
FIG. 1 illustrates an example of a detection kit including five detection sticks arranged in a detection kit, with a transparent cap removed from the detection kit.

FIG. 1 illustrates an example of a detection kit including five detection sticks arranged in a detection kit, with a transparent cap removed from the detection kit. Each of the detection sticks 16, 18 may comprise a flexible outer shell 21 containing one or more ampoules that are capable of being ruptured by a rupture mechanism, such as the segmented rupture mechanisms disclosed in the examples, below. When the ampoule or ampoules of the detection sticks are ruptured, the contents are released and are transported to the detection surface of the detection stick by way of wicking, gravity, capillarity or otherwise, such as by way of a wicking tip 23 inserted into the flexible outer shell 21. The detection surface of each detection stick may have an adhesive applied to the surface, which may be a porous layer 19 that covers the entire detection surface of one of the detection sticks 18 or may be provided in a pattern, such as the dots 17 shown on one detection sticks 16 of the detection kit 1. A latching mechanism 8 may be provided on the transparent cap 7, such that the cap becomes fixed on the body 5 of the detection kit 1, when the cap is snapped onto the body prior to rupturing of the ampoules. The latching mechanism 8 may be disposed on the inner side of the cap 7, such that it engages a notch 11 formed in the body 5 of the detection kit, for example. One or more such latching mechanisms may be provided on the cap, such that the cap can be initially removed for swabbing of the detection surfaces on a surface to be tested, but when rotated to the locking position with the arrows 9, 12 aligned, the cap locks into position on the body.

Figure 2:
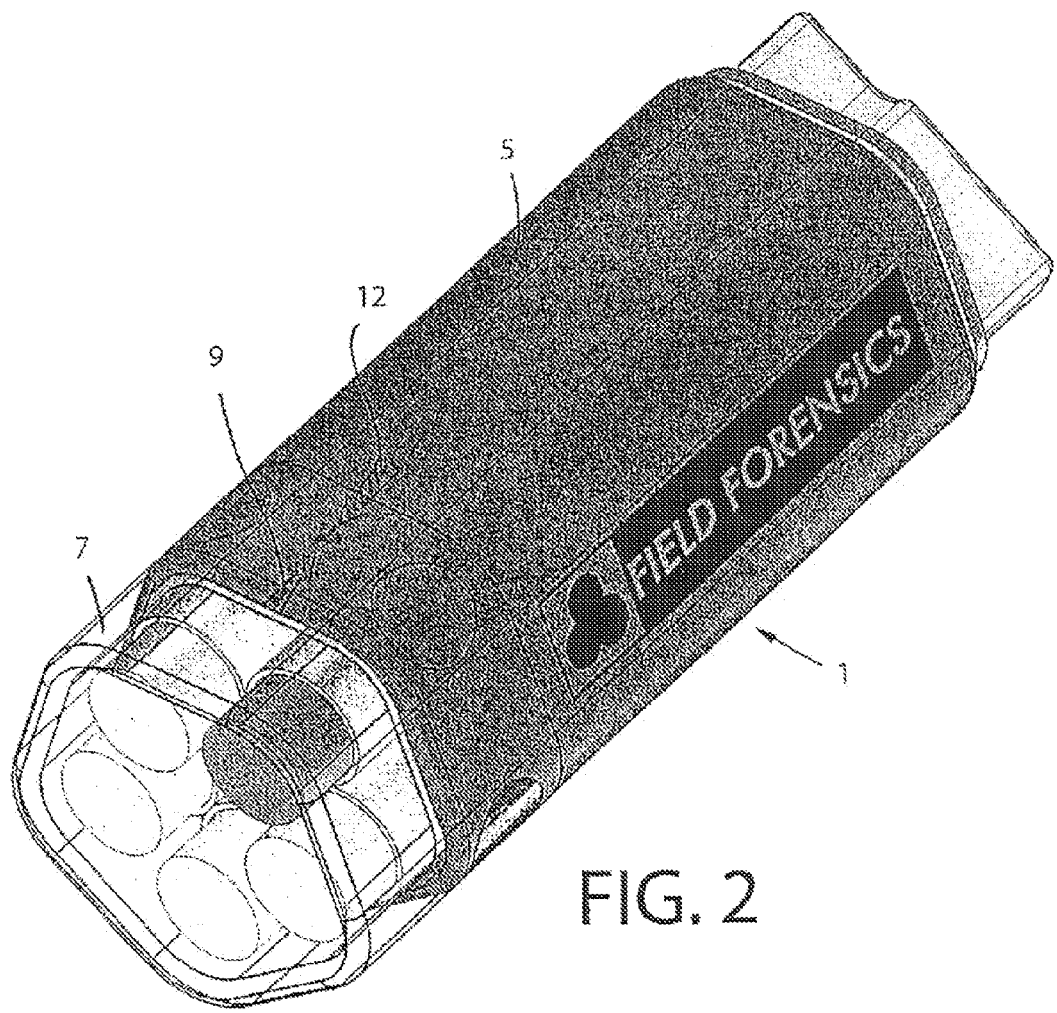
FIG. 2 illustrates the same detection kit with the transparent cap enclosing the detection kit, after the rupture of an ampoule, showing a color change indicating the presence of FIG. 3 illustrates the arrangement of five chambers within a partial view of the body of the detection kit for insertion of the five detection sticks and a central device for breaking of one or more ampoules in each of the detection sticks.

FIG. 2 illustrates the same detection kit with the transparent cap enclosing the detection kit, after the rupture of an ampoule, showing a color change indicating the presence of a compound to be detected. The arrows 9, 12 are aligned and the notch 11 is engaged with the latching mechanism 8.

Figure 3:
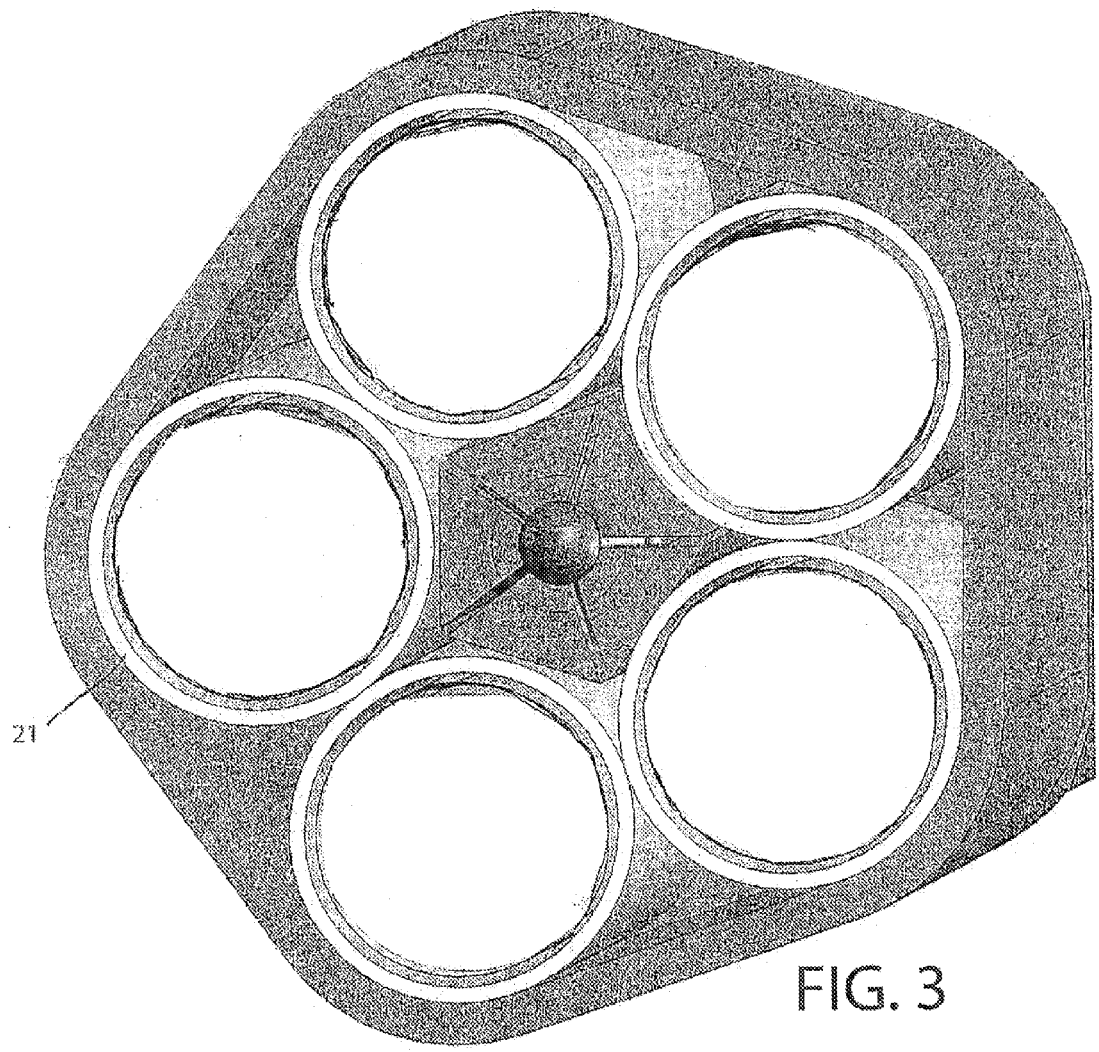

FIG. 3 illustrates the arrangement of five outer flexible shells 21 of five detection sticks within a partial view of the body 5 of a detection kit 1 and a central device for breaking of one or more ampoules in each of the detection sticks.

Figure 4A:
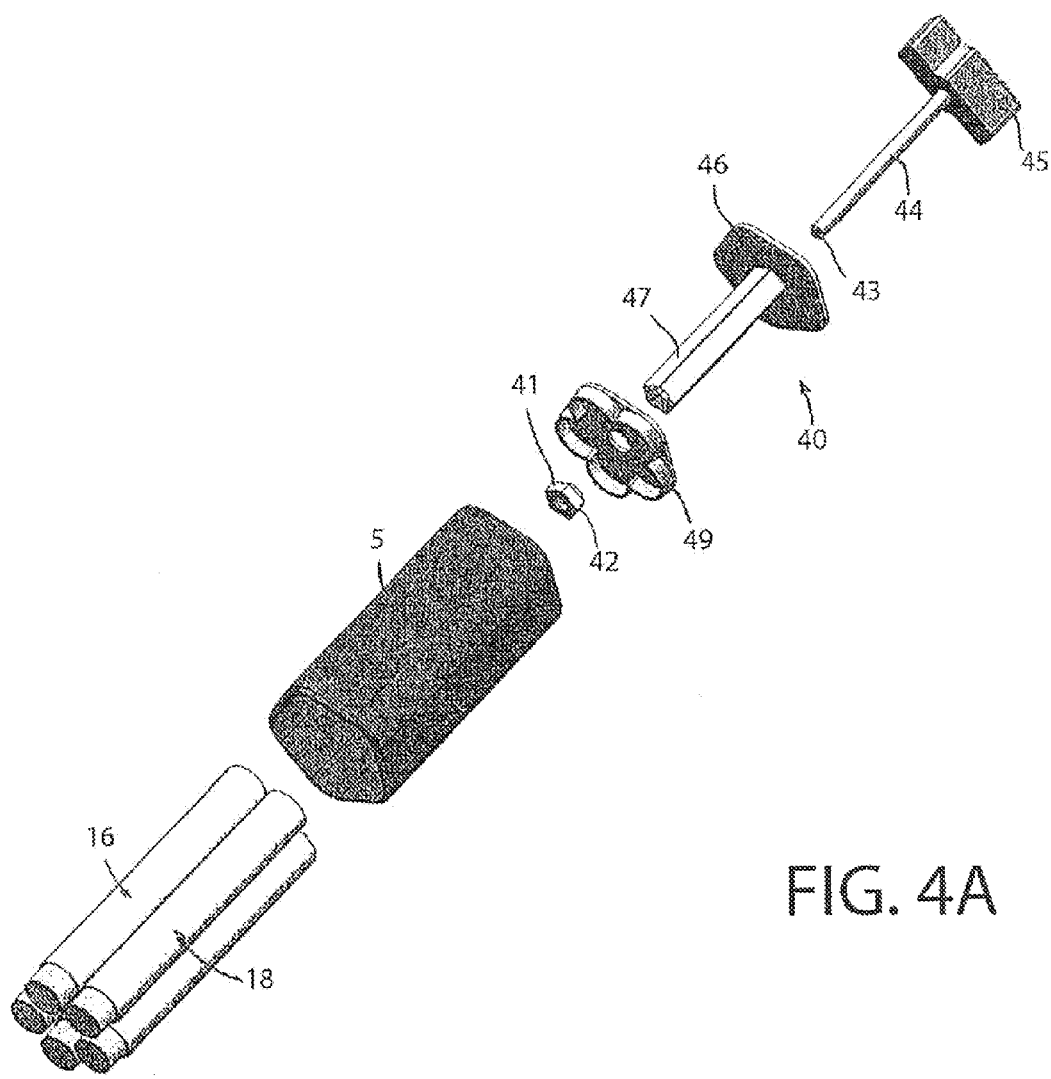
FIG. 4A illustrates an exploded view of the detection kit, absent the transparent cover, showing a rotary mechanism for breaking of the one or more ampoules in each of the five detection sticks.

FIG. 4A illustrates an exploded view of a detection kit 1, absent the transparent cover, showing a rotary mechanism for breaking one ampoule in each of the five detection sticks. A rupturing mechanism 40 is illustrated in an exploded view showing a spreading nut 41, having threaded inner surface 42 of a bore engageable by a threaded surface 43 on the end of a member 44 joined to a handle capable of being used for rotating the shaft. The threaded surface on the end of the member is threadingly engaged in the bore of the spreading nut, when the detection kit is assembled. In one example, the end of the member is engaged in the bore such that it is capable of rotating; moving the nut downward on the shaft, but the end is not disengageable from the nut by rotating in the opposite direction. For example, the shaft is first inserted through the bore of the nut, and the threaded end portion is then joined to the shaft prior to threadingly engaging the threaded end portion in the bore of the spreading nut. The spreading nut 41 is capable of engaging segmented rupture members 47 extending from a base 46, which may be plate-like. A detection stick retainer 49 may be provided with a hole for fitting over the rupture members 47 and may be shaped to accommodate a plurality of the detection sticks 16, 18. In one example, the detection sticks are adhered to the retainer 48, such as by gluing or potting the detection sticks within the retainer.

Figure 4B:
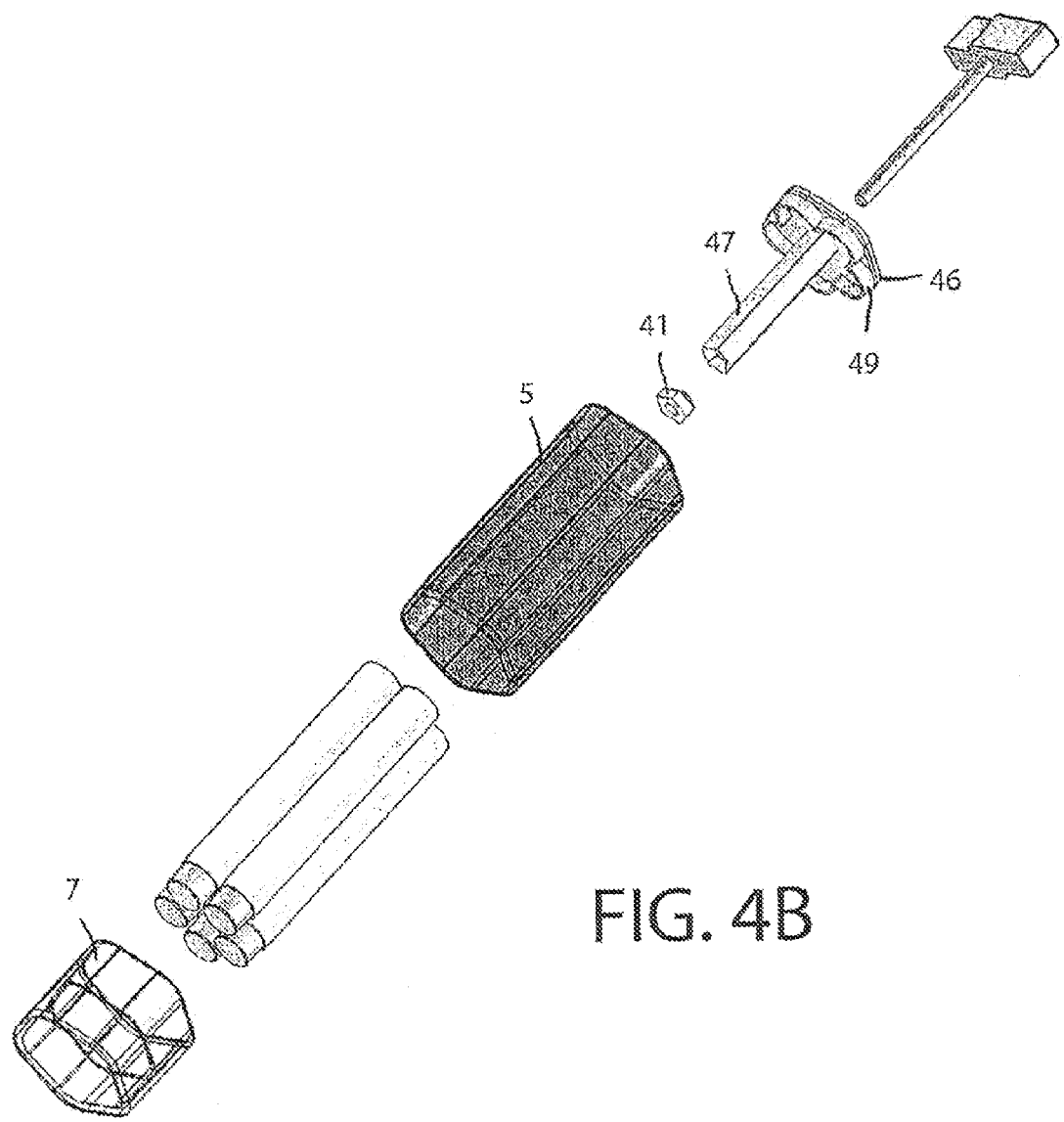
FIG. 4B illustrates an alternative example of a rotary mechanism similar to FIG. 4A.

FIG. 4B illustrates an alternative example of a rotary mechanism similar to FIG. 4A. In this example, the retainer 49 and base 46 are joined together. For example, the base and retainer may be adhered or integrally formed.

Figure 5B:
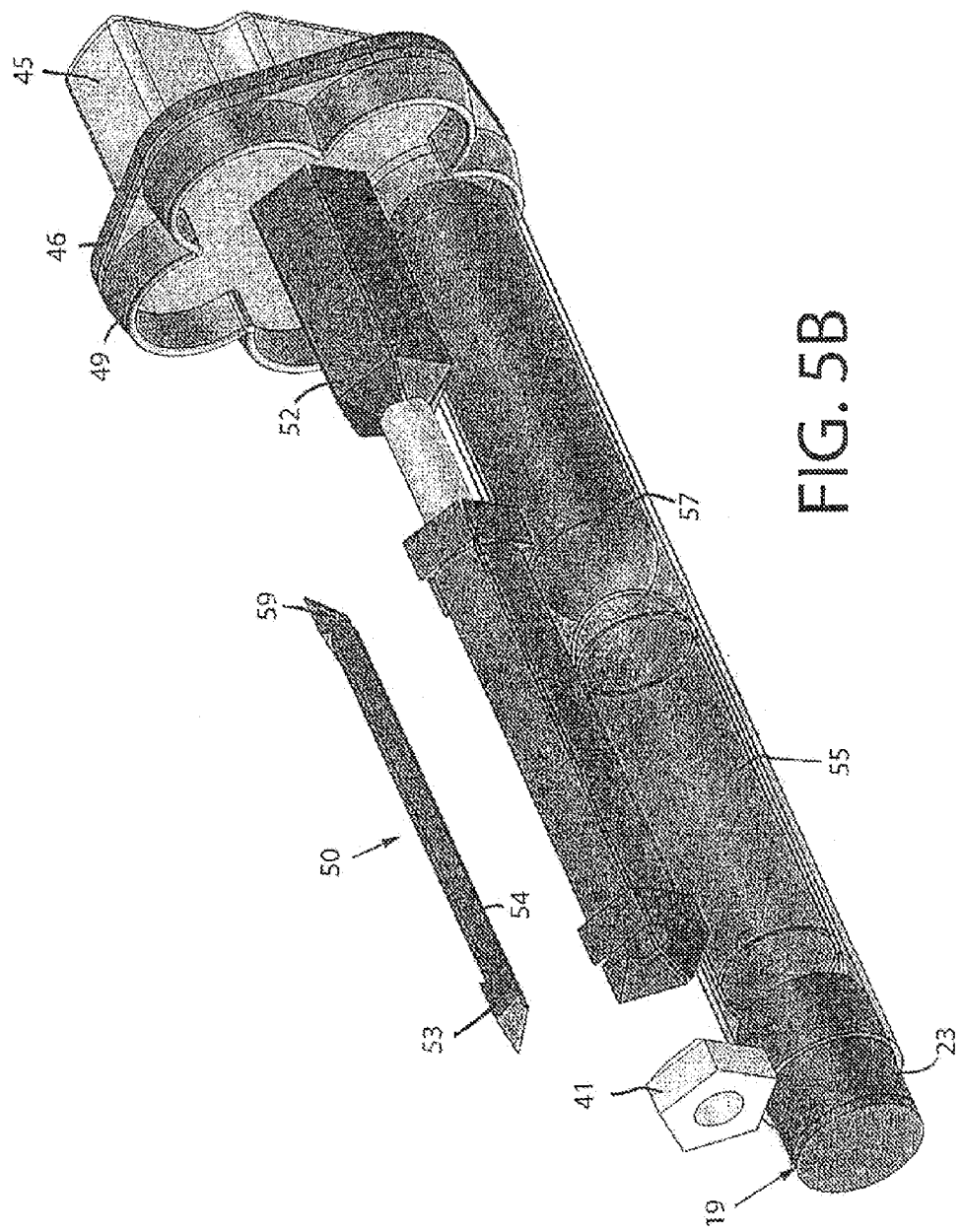

FIGS. 5A and 5B illustrate a single detection stick disposed in relation to a rotary mechanism shown in (A) a partial cutaway view and (B) a partially exploded cutaway view, which is similar to the examples in FIGS. 4A and 4B, except in FIG. 5 the rotary mechanism is design to rupture two ampoules in each detection stick by forcing both the top 53 and bottom 59 portions of the segmented rupture mechanism 50 to spread outwardly when the handle 45 of the rotary mechanism is rotated. A flexible sleeve 51 is shown in FIG. 5A, which holds individual segments 54 of the segmented rupture mechanism 50 together. The end 59 of the member attached to the handle 45 is shown extending beyond the nut 41. The spreading nut 41 spreadingly engages the end 53 of the rupture mechanism 50 when the handle is rotated. Also, the opposite end 59 engages a spreading post 52, which is fixedly attached to the base 46. resulting in the spreading of the opposite ends 59 of the segments 54 when the handle 45 is rotated. Thus the ends 53, 54 rupture both of the ampoules 55, 57 disposed in each of the plurality of detection kits, as shown in this example. The reactants mix and are transported to the wicking end 23 of the detection sticks 18 and through the adhesive layer 19 or to the powder or other compounds stuck to the patterned adhesive, for example. In FIG. 5B, the spreading post 52 is illustrated in an exploded view, showing the inclined surfaces at one end of the spreading post that engage similarly sloped surfaces of the opposite end 59 of the rupture mechanism 50.

Figure 6:
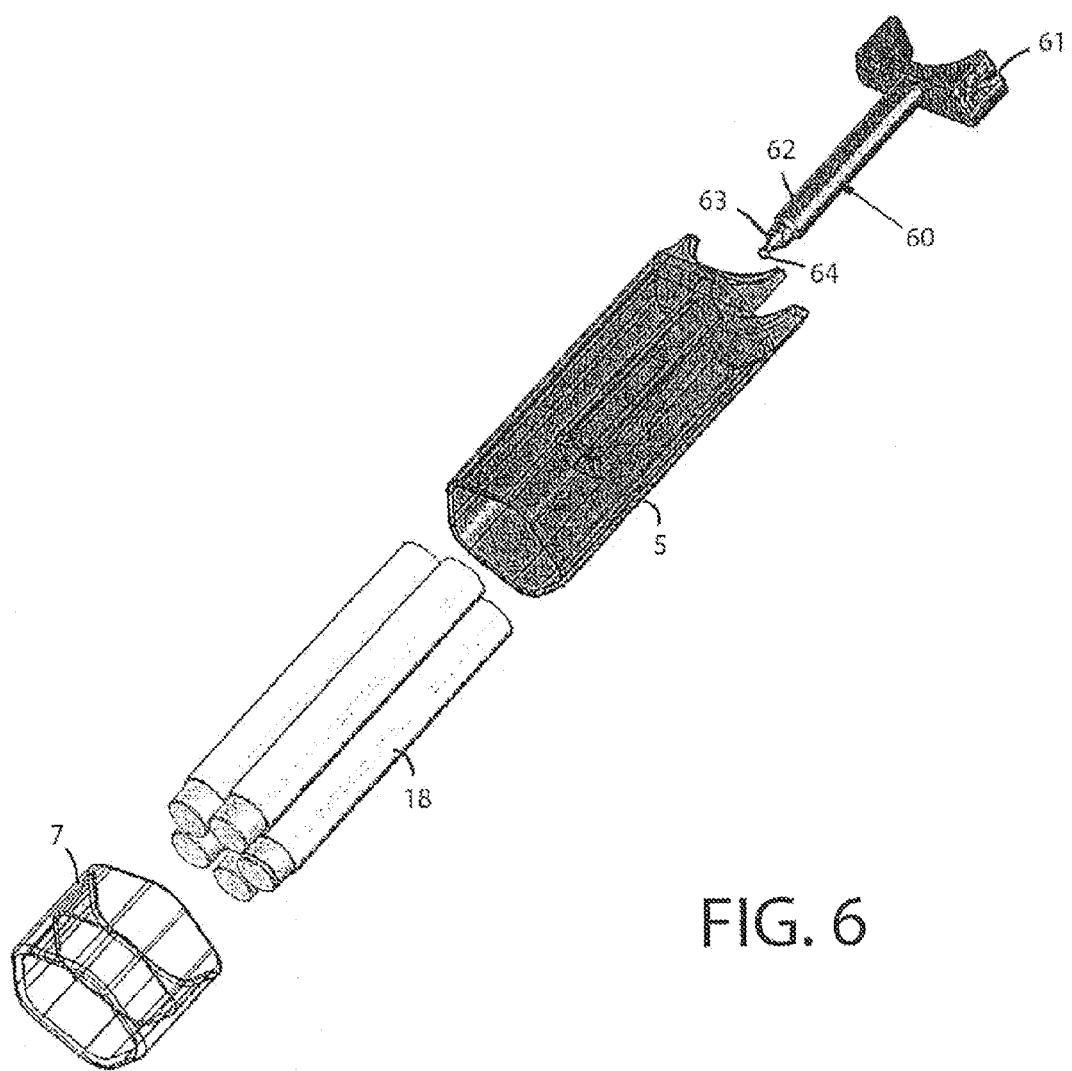
FIG. 6 illustrates an exploded view of the detection kit, showing a push button mechanism for breaking of the one or more ampoules in each of the five detection sticks.
Figure 7:
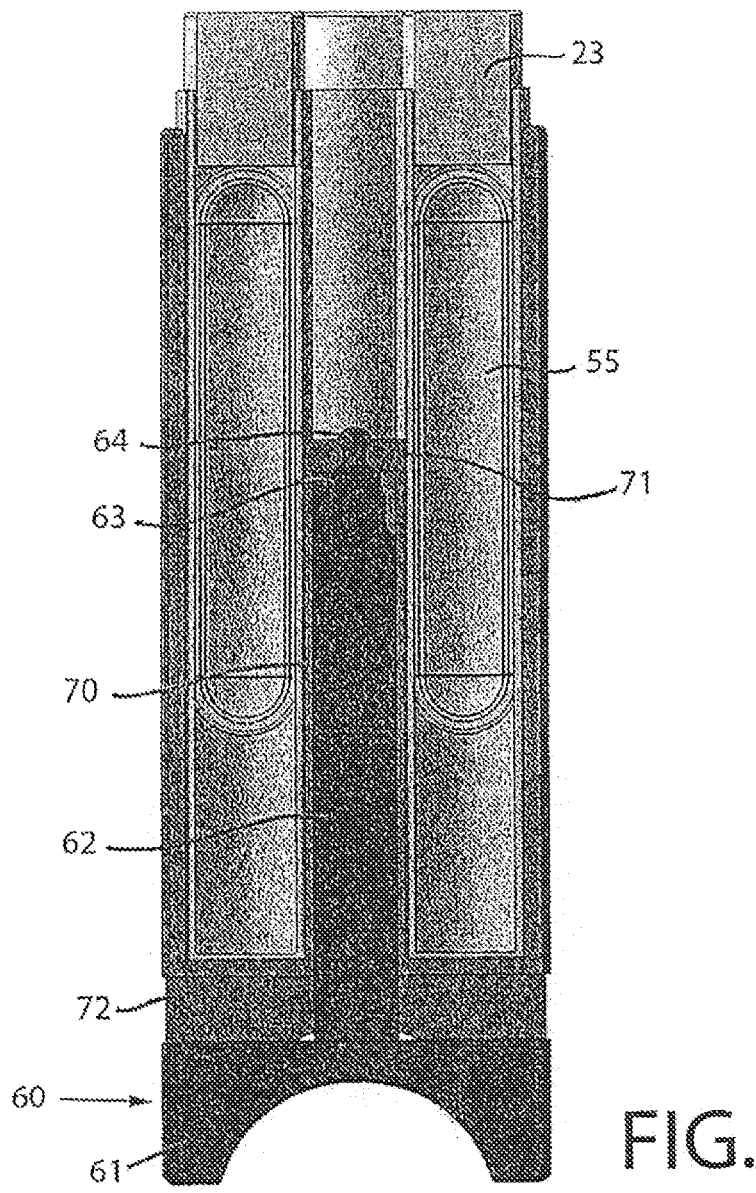
FIG. 7 illustrates a portion of the detection kit showing the mechanism for rupturing one or more of the ampoules of the detection sticks (two shown) in a first position.
Figure 8:
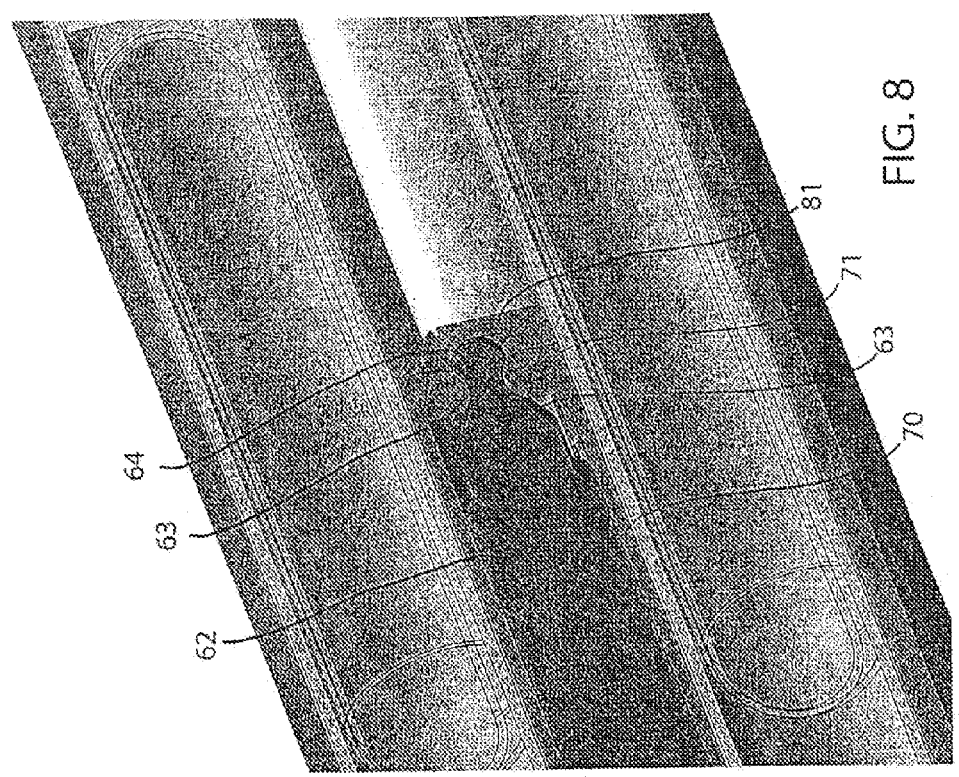
FIG. 8 illustrates an enlarged view of the example in FIG. 7.
Figure 9:
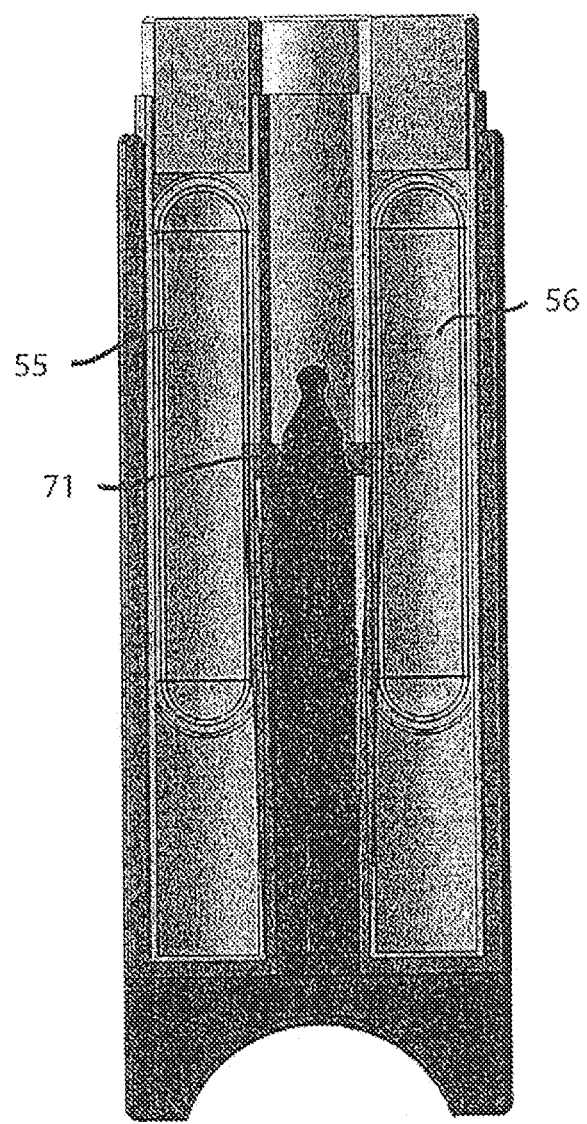
FIG. 9 illustrates the example of FIGS. 7 and 8 in a second position, after a segmented rupturing device, central to the five ampoules, is expanded, resulting in the rupture of one or more ampoules in the detection sticks (only two shown in this cutaway view).
Figure 10:
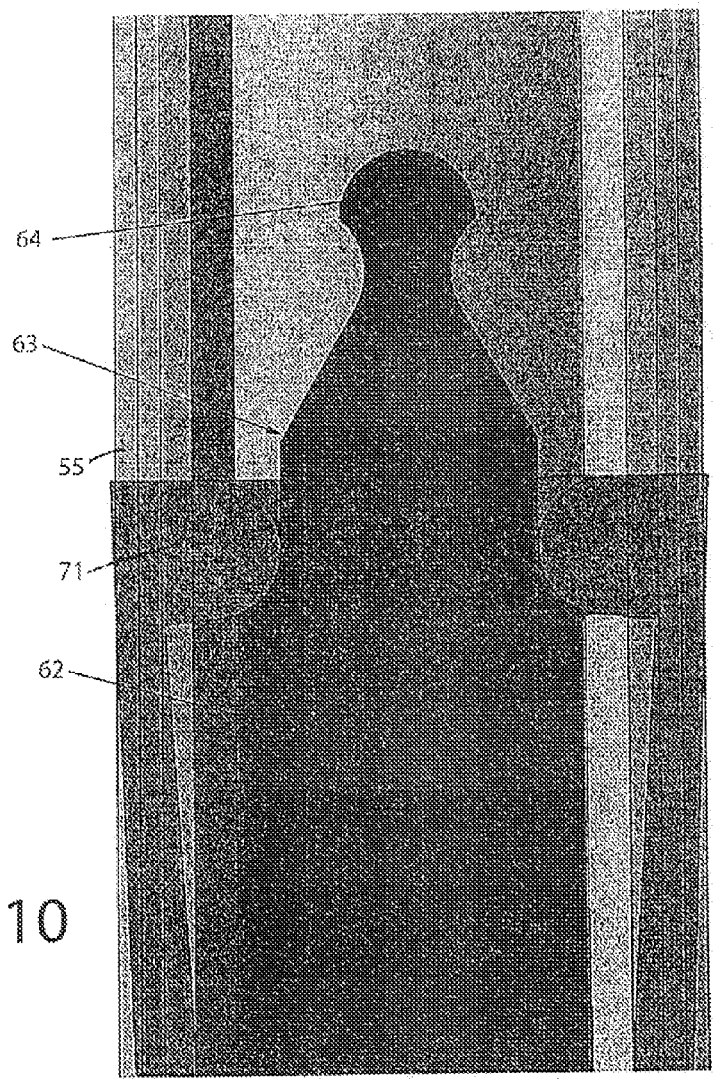
FIG. 10 illustrates an enlarged view of the example in FIG. 9.

FIG. 6 illustrates an exploded view of the detection kit, showing a push button plunger 60 for breaking of the one or more ampoules in each of the plurality of detection sticks 18. In this example, the rupture mechanism and base are integrally formed with the body 5 of the detection kit 1. The detection sticks are disposed in the body 5 and may be potted or otherwise fixed in the body. The plunger 60 may be integrally formed with a push button 61 on one end of a shaft 62 and a retention tip 64 on an opposite end of the shaft of the plunger 60. In FIG. 7, the retention end 64 is shown engaged with the rupture end 71 of the rupture mechanism 70. which is integrally formed with the body 5 of the detection kit 1. An expanding surface 63 is capable of spreading the rupture ends 71 of the segmented rupture mechanism 71, as illustrated in the drawing of FIG. 9. The retention end 64 is illustrated in a partial cross sectional, cutaway view in FIG. 8. In one example, the retention end is inserted through the rupture ends 71 prior to inserting disposing the plurality of detection sticks within the body of the kit. Then, the detection kits are disposed in the body of the kit, positively locking the plunger 60 in the kit. When the plunger is pressed, such as by the user's thumb, toward the body 5 of the kit, the inclined spreading surface 63 of the plunger engages the rupture ends 71 of the segmented rupture mechanism 70, forcing the ends 71 into contact with the ampoules and rupturing the ampoules, releasing the contents, such as reagents for detecting chemical compounds. In one example, a Griess reagent is used for detecting nitrates. In another example, 4-(dimethylamino)cinnamaldehyde (DMAC) is used for detecting urea nitrate. In yet another example, a molybdate reagent is used for phosphate detection. In still another example, Nessler reagent is used for the detection of ammonium nitrate or an ammonium ion thereof. For example, a combination of one or more of the foregoing may be used in a detection kit described in the examples. FIG. 10 shows a detailed view of the rupture ends 71 superimposed over the ampoules 55, showing that the ampoules would be ruptured when the plunger 60 is pressed.

Figure 11:
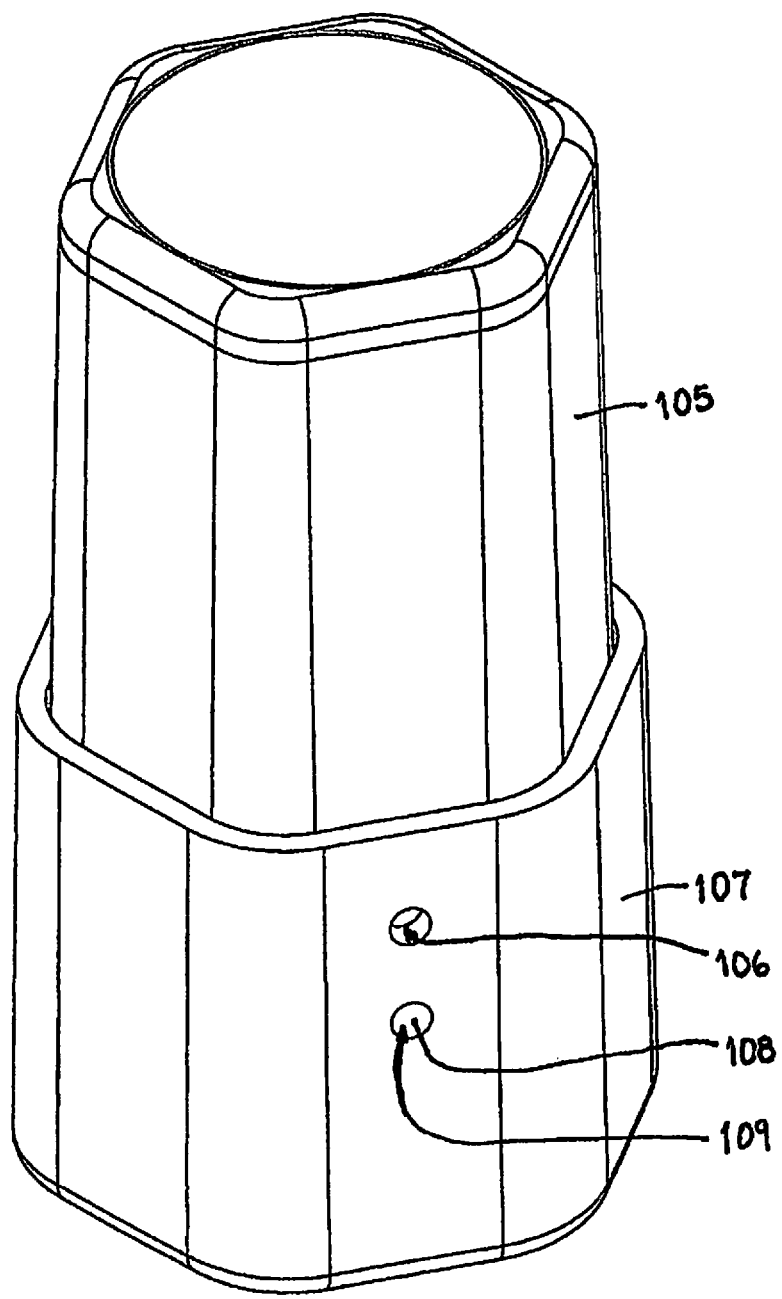
FIG. 11 illustrates an alterative example of a detection kit in a position causing rupture of one or more ampoules in the detection sticks.
Figure 12:
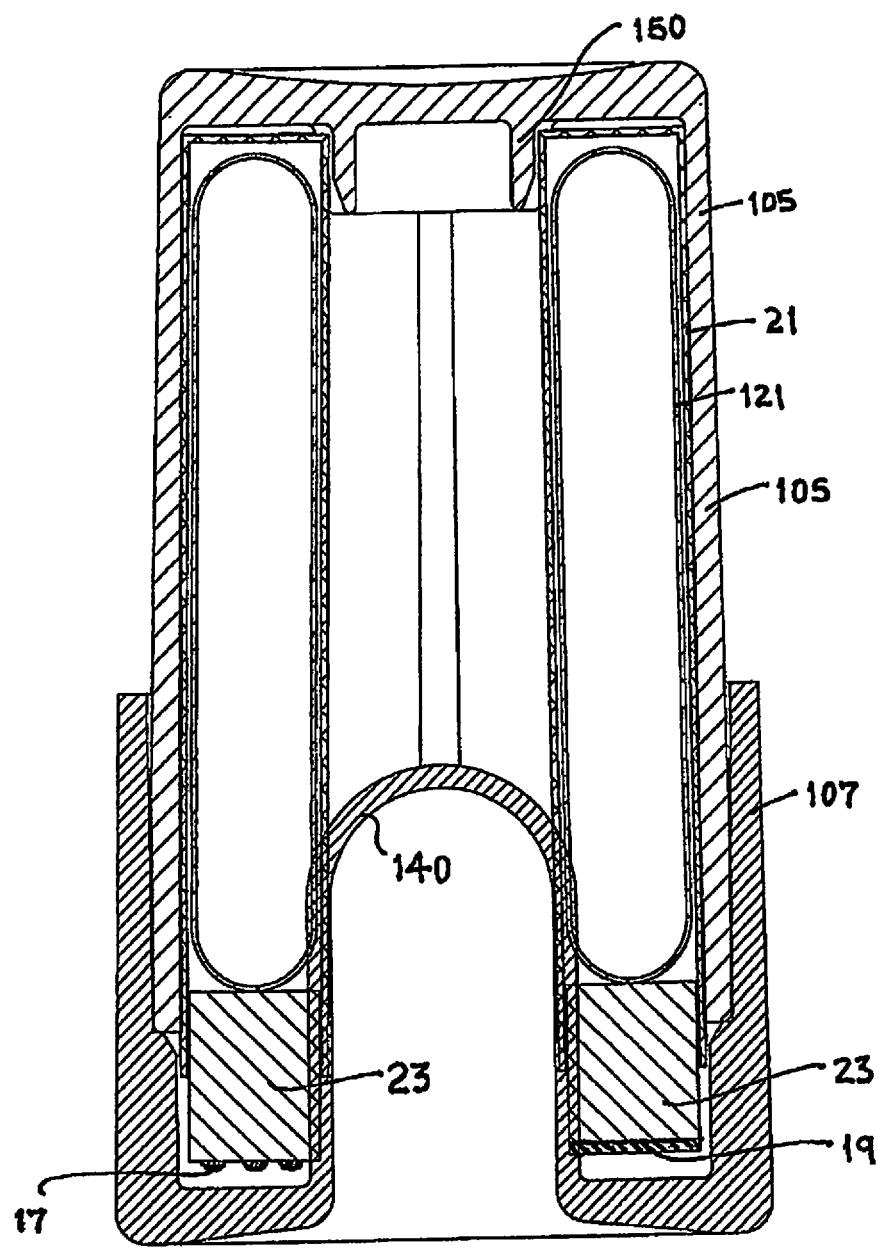
FIG. 12 illustrates a cross-sectional view of the example illustrated in FIG. 11.
Figure 14:
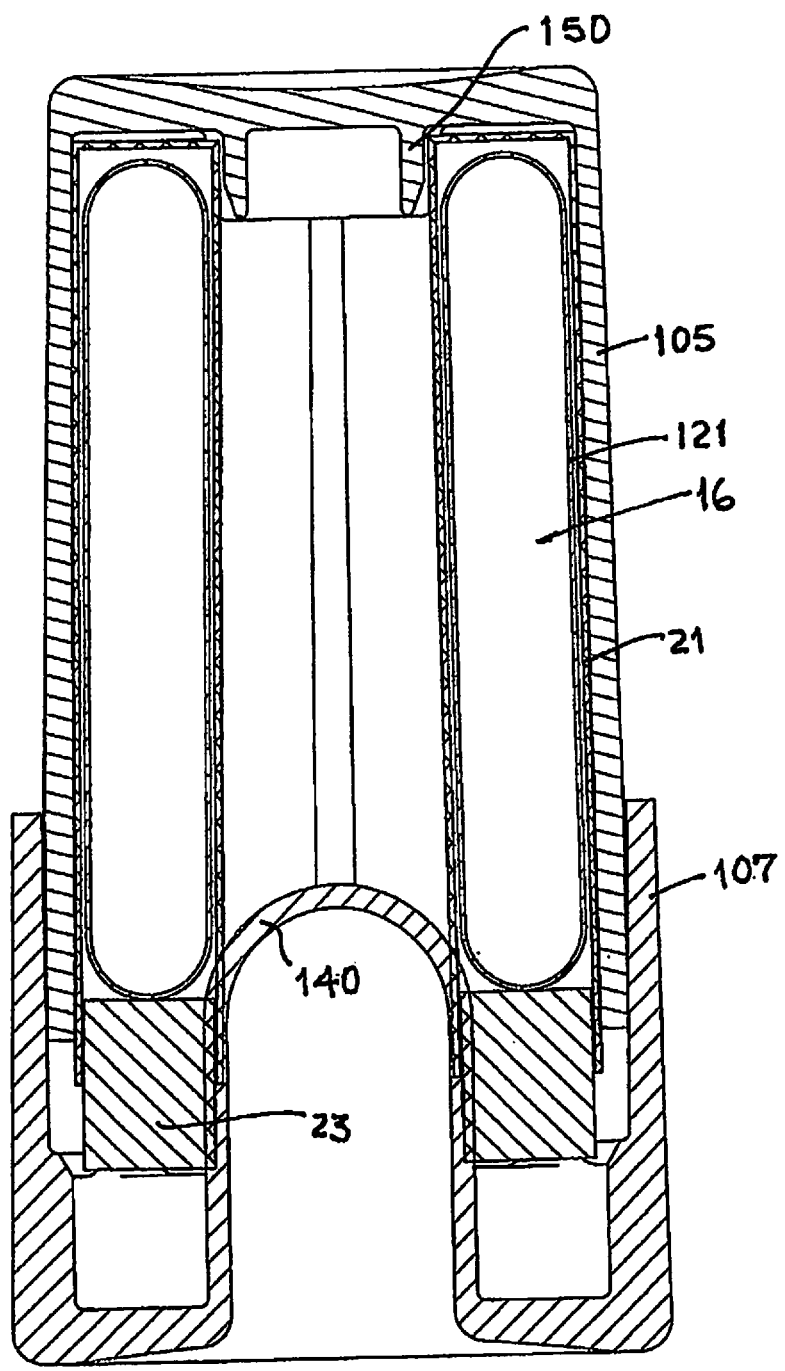
FIG. 14 illustrates the example of FIG. 11 in a first position, prior to rupture of one or more ampoules in the detection sticks.

FIG. 11 illustrates another example of a detection kit comprising a plurality of detection sticks. In this example, an integrated cap and rupture mechanism 107 fits conformingly over a housing 105 that contains the plurality of detection sticks. The cap 107 may be transparent to allow the visual detection of a color change on the end of one or more of the plurality of detection sticks. Two holes 106, 109 in the cap 107 may be engaged by a raised bump 108 disposed on a surface of the housing 105, providing a first position for the cap 107 prior to rupture of any ampoules of the detection sticks and a second position after compression of the cap 107 onto the housing 105 between a thumb and a finger of a user to cause the ampoules to rupture. As illustrated in the example of FIG. 12, an ampoule 121 within a flexible sleeve 21 is capable of being ruptured by a rupture mechanism 140 arranged such that the rupture mechanism 140 squeezes each of a plurality of ampoules 121 between the inner wall of the housing 105 and the rupture mechanism 140, when the cap 107 is compressively engaged on the housing 105, moving the cap 107 from a first position illustrated in FIG. 14 to the rupture position illustrated in FIG. 12. An ampoule releases one or more fluids, such as a reagent or solvent or both a reagent and solvent, that may be wicked by the wicking tip 23 to a porous adhesive layer 19 or to adhesive dots 17, for example. The adhesive layer or dots may be disposed on a surface of the wicking tip 23, with "on" being defined broadly to mean in contact with a surface of the wicking tip 23 and may be adhesively adhered to the surface. Preferably, the adhesive layer and dots are tacky and capture powders, particles and other contaminants located on a surface swabbed by the plurality of wicking tips 23. Each ampoule may have one or more volumes for containing the one or more fluids, which may be either premixed or separated, such as in breakable ampoules.

Figure 13:
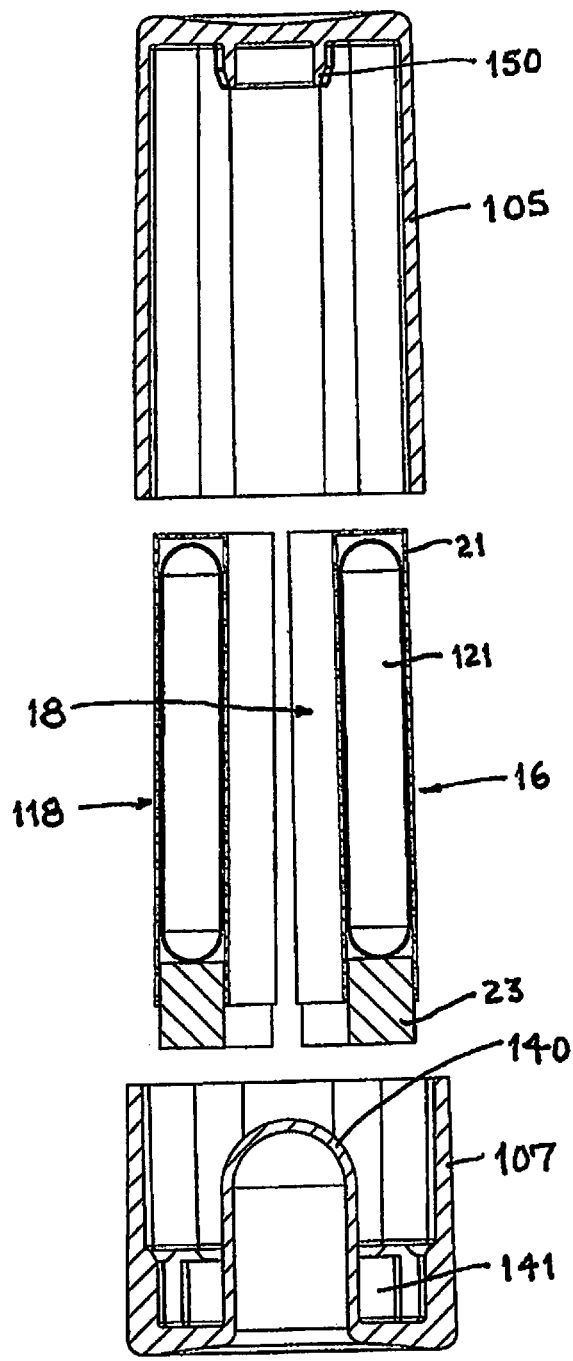
FIG. 13 illustrates a partially-exploded, cross-sectional view of the example illustrated in FIG. 11, identifying a housing, one or more detection sticks (only two oppositely disposed detection sticks shown in this cross-sectional view), and an integrally-formed displaceable cap and ampoule crushing mechanism.

For example, separate detector sticks 16, 18, 118 are illustrated in FIG. 13, each having a single, separate ampoule 121, for example. Alternatively, more than one ampoule may be coupled together to contain more than one fluid separated from the other. One detector stick 18 in the partial cross-sectional view of FIG. 13 is illustrated disposed partially obscured behind a cross-sectional view of a detector stick 16, for example, in an arrangement accommodating six detector sticks. The cap 107 comprises an integrated rupture mechanism 140 and dividers 141 dividing the wicking tip 23 of one detector stick 16 from the wicking tip 23 of the adjacent detector stick 18, for example. The integrated dividers 141 may prevent mixing of fluids from one ruptured ampoule 121 with a neighboring ruptured ampoule in the adjacent detector stick 18.

Figure 15:
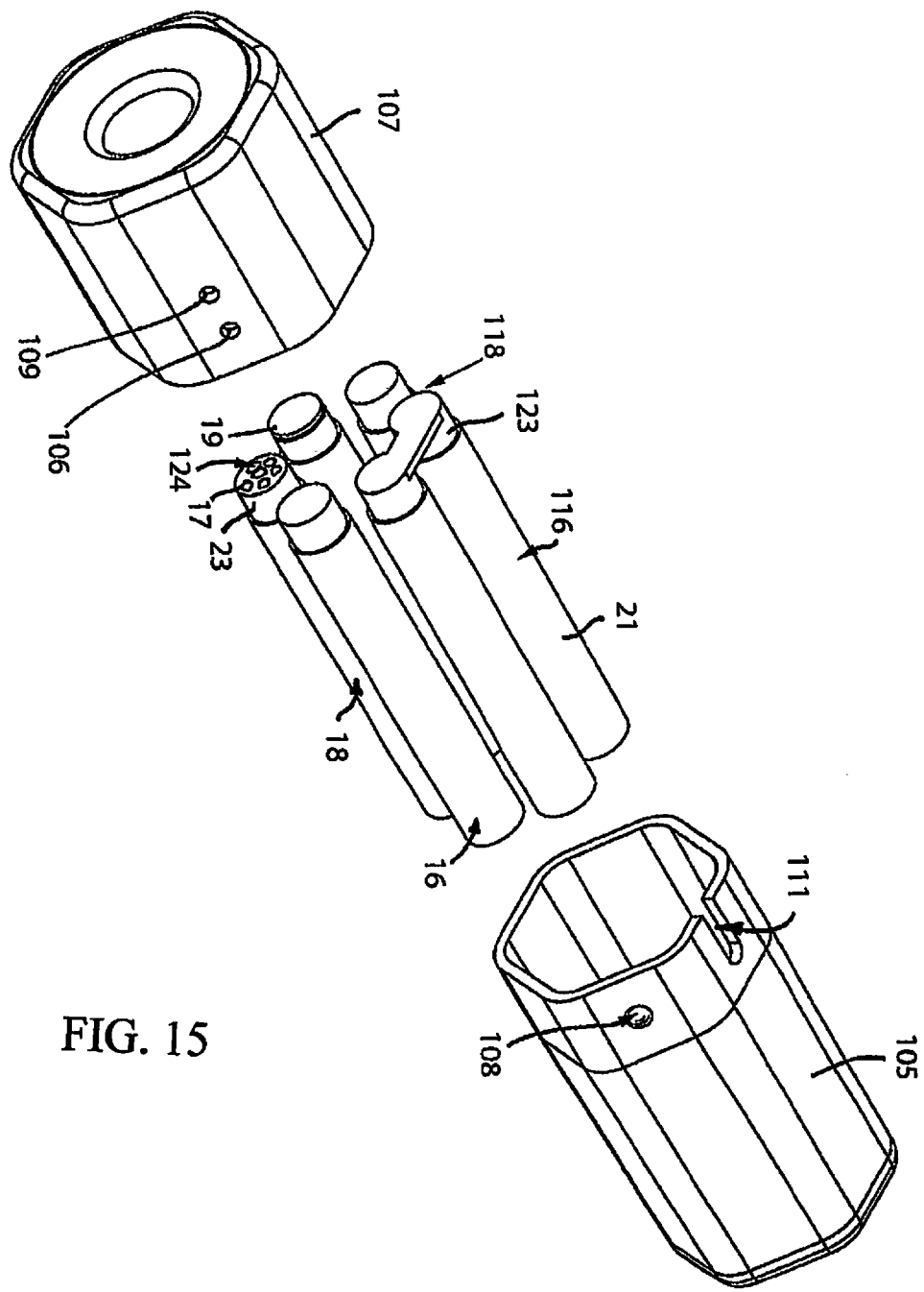
FIG. 15 illustrates an exploded, perspective view of an example having six detection sticks, two of the six detection sticks having a co-joined wicking swab.

The illustration of FIG. 15 shows an arrangement of six detector sticks, as arranged in a single housing 105, for example. A slot 111 may be aligned with protrusion on the cap 107, such that the cap 107 may only be aligned in one way. For example, this may be necessary if a pair of adjacent detector sticks 116 have wicking tips 123 joined together. For example, two different fluids may be disposed in two different ampoules, which may mix when wicked by the wicking tip 123 to the co-joined detection surface of the pair of adjacent detector sticks 116. Two or more detector sticks may be joined together for presenting a plurality of reagents and/or solvents as necessary to induce a visual change on the surface of the detector sticks, when a target chemical is present at the surface due to swabbing of the surface of the wicking tip on a contaminated surface, for example.

Target compounds may include drugs, explosives or precursors of compounds that may be combined, such as urea nitrate, ammonium nitrate, other nitrates, urea, phosphate fertilizers and the like. The housing may be made of a low density polyethylene, may be opaque and/or may have instructions. An instruction sheet may include a peel-off label for annotation of date, time, location, conditions and the like. The cap may be a transparent plastic material, such as a polycarbonate, acrylic, urethane or the like, such that the detection surfaces of the detector sticks are visible through the cap. The housing may have color indicators identified in relation to the physical location of detection surfaces of the detector sticks, such that the user can quickly compare the detection surface to the color indicator to determine if there is a positive indication for the presence of one of the target compounds, for example. The detection surfaces may have an adhesive, either a porous layer or dots of adhesive, and/or a solid or gel reagent immobilized on the detection surface. The solid or gel reagent may be capable of directly detecting liquid, mist or vapor phase compounds. A solvent, such as alcohol, water or the like, or a liquid reagent could be released by the rupture of a reservoir in the detection sticks, for example, which could lead to a reaction at the detection surface by the solid phase reagent and a target compound or a liquid phase reagent and a target compound or a plurality of reagents, solid and/or liquid, and one or more target compounds, for example.

Figure 16:
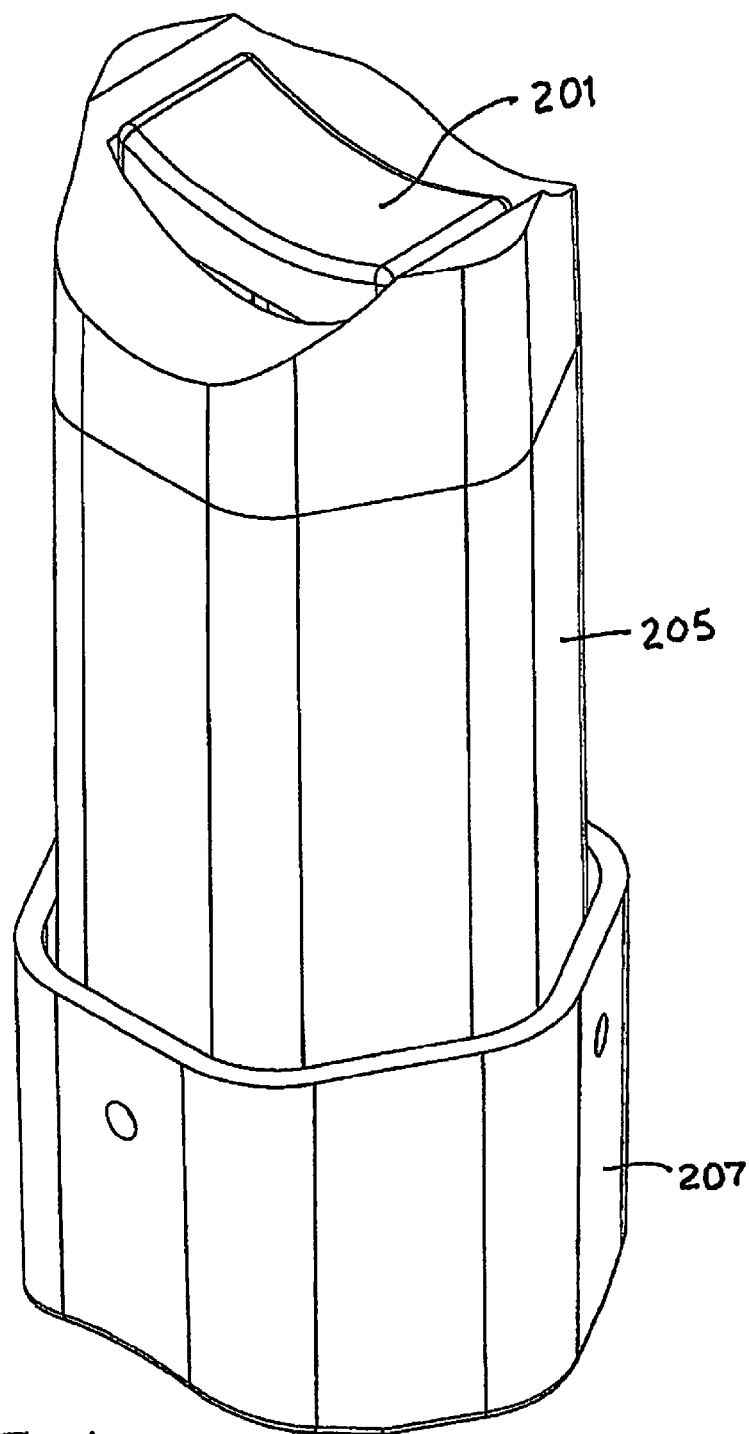
FIG. 16 illustrates another example of an assembled detection kit.
Figure 17:
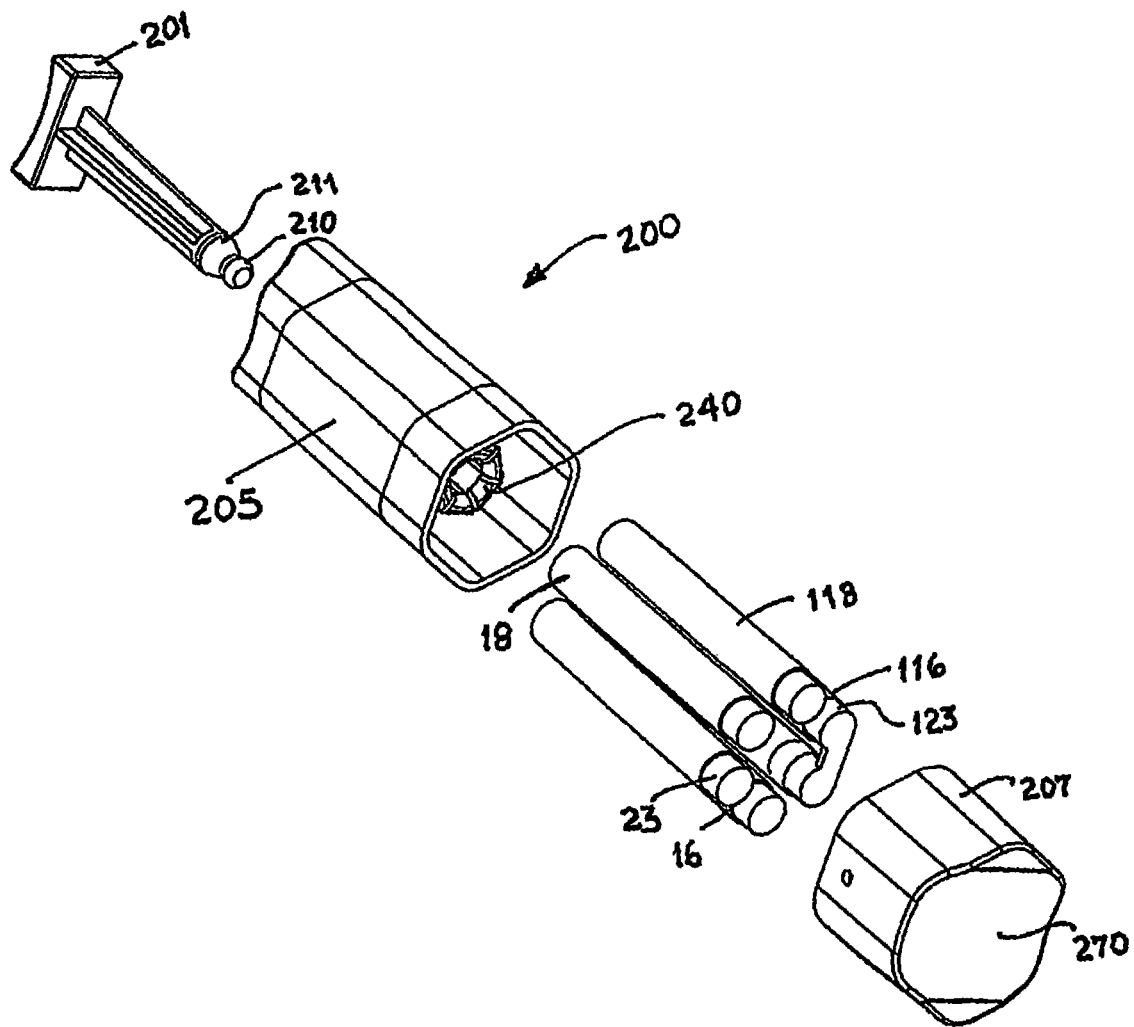
FIG. 17 illustrates an exploded, perspective view of the example in FIG. 16.
Figure 19:
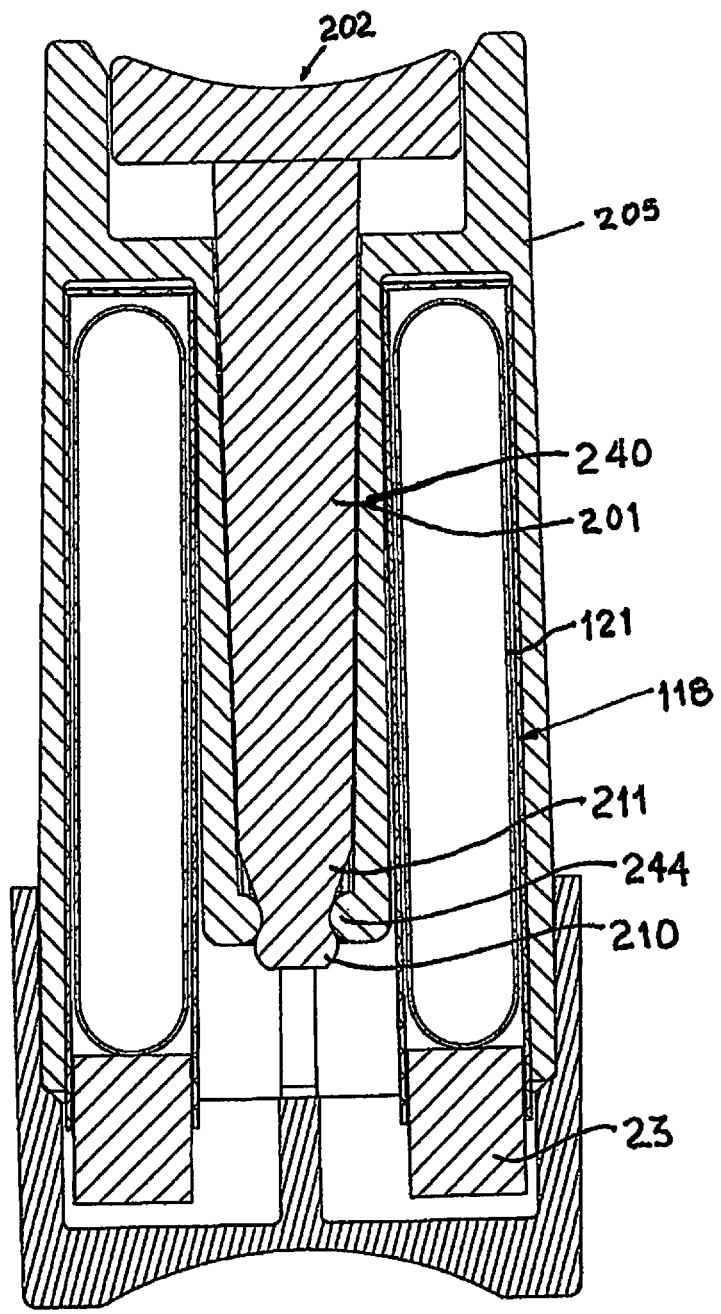
FIG. 19 illustrates a cross-sectional view of the assembled detection kit in FIG. 16.

FIG. 16 illustrates yet another example, using a push rod 201 to activate rupture of a rupture mechanism 240, for example. FIG. 17 illustrates an exploded, perspective view of a detector kit 200 showing the push rod 201 insertable into a rupture mechanism 240 integrally molded with the housing 205. Six detector sticks are arranged circumferentially within the housing 205 around the rupture mechanism 240. A cap 207 includes an ergonomically-shaped compression surface 270 shaped to accommodate a thumb, finger or fingers within a concave cavity. The cap 207 may be transparent to allow visual observation of a change in color or other indication of the presence or absence of a particular contaminant, such as based on a chemical reaction between a target composition and a reagent, solvent or the like provided by the detector kit 200. The push rod 201 may have an ergonomical compression surface 202, such as the concave shape illustrated in FIG. 18, for example. A bulbous tip 210 engages a constriction 244 of the rupture mechanism 201, as illustrated in FIG. 19, retaining the push rod 201 within the detector 200, during storage and transport, for example. The rupture mechanism 240 comprises a plurality of fingers 242 preferably numbered and arranged to contact each of a plurality of the detector sticks when plunged into the detector 200 under compression by a user of the kit. For example, a slit 241 may separate each of the plurality of fingers 242, allowing the flexibility of the fingers to bend radially outwardly. When the push rod 201 is plunged by compression of the concave surface 270 of the push rod 201 toward the concave surface 270 of the cap 207, such as by compressing between a thumb and one or more fingers of a user's hand, then a conically-shaped portion 211 of the push rod 201 engages the constriction 244 of the rupture mechanism 240 forcing the fingers 242 of the rupture mechanism 240 radially outward, contacting and rupturing each of the plurality of ampoules 121 in each of the detector sticks 118, for example.

As in the previous examples, simultaneous rupturing of each of the ampoules releases a fluid that is wicked by the wicking tips 23 to the detection surfaces that are swabbed on or across surfaces that may have the presence of one or more target compositions that are to be detected, if present. The cap 207 may include dividers, as in the other examples, which may prevent cross-contamination of fluids from one wicking tip 23 to another. Alternatively, two or more wicking tips may be joined to encourage the transfer of fluid from one wicking tip to the other.

The claims are not limited to the examples, and features of the examples may be combined or modified by a person having ordinary skill in the art, based on this description and the drawings provided. The examples are provided to show various arrangements and features, and the arrangement and features in one example may be combined with the arrangement and features of other examples. For example, the ergonomically designed cap and housing of one example may be implemented in the other examples without undue experimentation, based on teachings provided in this disclosure.

What is claimed is:

1. A detection kit for detecting a target compound or target compounds comprises:
   a plurality of sticks, each stick comprising: an outer sheath, a wicking tip, a detection surface and a breakable ampoule enclosing a volume of a fluid;
   an outer housing containing the plurality of sticks;
   a rupture mechanism; and
   a removable cap comprising a transparent material, the cap being mated with the outer housing, such that the detection surface of each of the sticks is exposed when the cap is removed, and when the cap is matingly engaged on the outer housing, the detection surface of each of the sticks are enclosed within the housing and the cap and are visible through the transparent cap;
   wherein the detection surface of each of the plurality of sticks is disposed on the wicking tip arranged such that the wicking tip is capable of directing the fluid to the detection surface by wicking of the fluid from the volume, when the fluid is released by activating the rupture mechanism;
   wherein the fluid comprises a solvent, a reagent or a combination of a solvent and a reagent;
   wherein the volume of the fluid is contained within the outer sheath, such that when the fluid is released from the volume, the outer sheath contains the fluid within the stick, whereby the fluid is wicked by the wicking tip from a first end of the wicking tip to the detection surface on an opposite end of the wicking tip;
   wherein the outer sheath is of a polymer;
   wherein the detection surface comprises an adhesive.

2. The kit of claim 1, wherein the detection surface further comprises a solid phase reagent.

3. The kit of claim 2, wherein the fluid comprises a solvent.

4. The kit of claim 3, wherein the rupture mechanism is an integrally-formed portion of the cap.

5. The kit of claim 4, wherein the integrally-formed portion of the cap comprises an inwardly directed surface from a top portion of the cap capable of contacting and breaking each of the breakable ampoules of the plurality of sticks, when the cap and the housing are compressed, displacing the top portion of the cap toward the housing.

6. The kit of claim 5, wherein the inwardly directed surface includes a hemispherical shell extending from an annular wall, the annular wall extending from the top portion of the cap.

7. A detection kit for detecting a target compound or target compounds comprises:
   a plurality of sticks, each stick comprising: an outer sheath, a wicking tip, a detection surface and a volume of a fluid;
   an outer housing containing the plurality of sticks;
   a rupture mechanism; and
   a removable cap comprising a transparent material, the cap being mated with the outer housing, such that the detection surface of each of the sticks is exposed when the cap is removed, and when the cap is matingly engaged on the outer housing, the detection surface of each of the sticks are enclosed within the housing and the cap and are visible through the transparent cap;
   wherein the detection surface of each of the plurality of sticks is disposed on the wicking tip arranged such that the wicking tip is capable of directing the fluid to the detection surface by wicking of the fluid from the volume, when the fluid is released by activating the rupture mechanism;
   wherein the fluid comprises a solvent, a reagent or a combination of a solvent and a reagent;
   wherein the volume of the fluid is contained within the outer sheath, such that when the fluid is released from the volume, the outer sheath contains the fluid within the stick, whereby the fluid is wicked by the wicking tip from a first end of the wicking tip to the detection surface on an opposite end of the wicking tip;
   wherein the detection surface comprises an adhesive.

8. The kit of claim 7, wherein the adhesive is applied as a porous adhesive layer extending over a substantial portion of the wicking tip.

9. The kit of claim 8, wherein the porous adhesive layer includes a solid phase reagent on the surface of the porous adhesive layer.

10. The kit of claim 9, wherein the detection surface comprises a solid phase reagent.

11. The kit of claim 10, wherein the fluid comprises a solvent.

12. The kit of claim 1, wherein the rupture mechanism comprises an integrally-formed portion of the cap.

13. The kit of claim 12, wherein the integrally-formed portion of the cap comprises an inwardly directed surface from a top portion of the cap capable of contacting and breaking each of the breakable ampoules of the plurality of sticks, when the cap and the housing are compressed, displacing the top portion of the cap toward the housing.

14. The kit of claim 13, wherein the inwardly directed surface includes a hemispherical shell extending from an annular wall, the annular wall extending from the top portion of the cap.

15. The kit of claim 1, wherein the rupture mechanism comprises an integrally-formed portion of the housing, and a push rod deflects a portion of the rupture mechanism radially outward, when the push rod is compressed toward the housing, such that the rupture mechanism is capable of contacting and radially compressing the outer sheath, releasing the fluid from the volume of each of the plurality of sticks.

16. The kit of claim 1, wherein the rupture mechanism comprises a rotatably activatable mechanism capable of contacting and radially compressing the outer sheath between the rupture mechanism and the housing, releasing the fluid from the volume of each of the plurality of sticks.

17. The kit of claim 16, wherein at least one of the plurality of sticks comprises a plurality of volumes separating at least two different fluids within the at least one of the plurality of sticks.

18. The kit of claim 1, wherein the plurality of sticks comprises at least five sticks.

19. The kit of claim 18, wherein the plurality of sticks comprises six sticks, and the six sticks are arranged circumferentially within the housing.

20. The kit of claim 7, wherein two or more of the detection surfaces of the plurality of sticks are joined one to the other, such that the fluid of a first of the plurality of sticks comprising a first of the two or more adjacent detection surfaces mixes with the fluid of a second of the plurality of sticks comprising a second of the two or more adjacent detection surfaces.

21. A method of detecting a plurality of target compounds, comprising:
   selecting a detection kit according to claim 7;
   removing the cap;
   swabbing the detection surface of each of the sticks on a target surface;
   replacing the cap;
   activating the rupture mechanism;

releasing the fluid from the volume of each of the plurality of sticks, at the same time by activating the rupture mechanism, such that the fluid of each of the plurality of sticks displaces to the detection surface of each of the plurality of sticks, respectively; and checking the detection surface of each of the plurality of sticks, determining if any of the plurality of target compounds is present on the detection surface of any of the plurality of sticks.

* * * * *